United States Patent

Panzeri et al.

[11] Patent Number: 6,121,449
[45] Date of Patent: Sep. 19, 2000

[54] PROCESS FOR PREPARING CARBOXAMIDO-4-AZASTEROIDS

[75] Inventors: Achille Panzeri, Merate; Matteo D'Anello, Cormano; Antonio Longo; Marcella Nesi, both of Milan, all of Italy

[73] Assignee: Pharmacia & Upjohn SpA, Milan, Italy

[21] Appl. No.: 09/367,847

[22] PCT Filed: Dec. 17, 1998

[86] PCT No.: PCT/EP98/08527

§ 371 Date: Aug. 27, 1999

§ 102(e) Date: Aug. 27, 1999

[87] PCT Pub. No.: WO99/35161

PCT Pub. Date: Jul. 15, 1999

[30] Foreign Application Priority Data

Dec. 31, 1997 [GB] United Kingdom .................... 9727522

[51] Int. Cl.⁷ .................................................. C07D 221/02
[52] U.S. Cl. .................................. 546/77; 546/61; 546/26
[58] Field of Search ................................................ 546/77

[56] References Cited

U.S. PATENT DOCUMENTS

| | | | |
|---|---|---|---|
| 5,155,107 | 10/1992 | Panzeri et al. | 514/232.8 |
| 5,342,948 | 8/1994 | Panzeri et al. | 546/77 |
| 5,407,939 | 4/1995 | Panzeri et al. | 514/284 |
| 5,418,238 | 5/1995 | Panzeri et al. | 514/284 |
| 5,719,159 | 2/1998 | Panzeri et al. | 514/284 |

*Primary Examiner*—Jose' G. Dees
*Assistant Examiner*—Sabiha N. Qazi
*Attorney, Agent, or Firm*—Oblon, Spivak, McClelland, Maier & Neustadt, P.C.

[57] ABSTRACT

A process for producing a compound of formula (I):

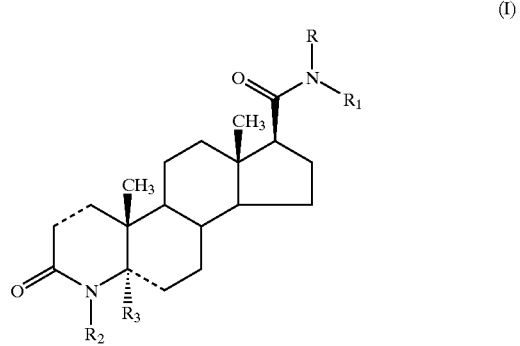

wherein the dotted lines - - - independently represent a single or double bond and R, $R_1$, $R_2$ and $R_3$ are each hydrogen or an organic radical, comprises treating the corresponding 17β-carbonylimidazole intermediates with anhydrous acids in the presence of an amine and, optionally, hydrogenating the resulting compound.

8 Claims, No Drawings

PROCESS FOR PREPARING CARBOXAMIDO-4-AZASTEROIDS

The present invention refers to a process for preparing carboxamido-4-azasteroids and, more in particular, it relates to a process for preparing 17β-carboxamido-4-azasteroids starting from the corresponding 17β-carbonylimidazole derivatives.

Carboxamido-4-azasteroids such as, for instance, 17β-carboxamido-4-aza-5α-androstan-3-ones and related unsaturated androstenones or androstadienones derivatives are compounds known in the art to be endowed with pharmacological activity, i.e. testosterone 5α-reductase inhibitory activity, and are thus useful in therapy in the treatment of hyperandrogenic conditions.

For a general reference to the pharmacological activity of the said compounds see, for instance, EP-A-0271220, WO 94/03475 and Current Pharmaceutical Design, 1996, 2, 59–84. Several processes for preparing carboxamido-4-azasteroids are known in the literature.

For instance, as reported in the international patent application WO 94/03475 in the name of the applicant, 17β-carboxamido-4-azasteroids are prepared by reacting a properly activated 17β-carboxy-4-azasteroid with a suitable amine.

Properly activated carboxy groups forming amide bonds include, for instance, acyl chlorides, thioesters, hydroxybenzotriazole esters, mixed anhydrides and acyl-imidazole derivatives.

Although suitable to form amide bonds, most of these activating groups cannot be used to prepare carboxamido-4-azasteroids because reacting with the N-atom of the azasteroid moiety or, if present, with the double bond in position 5,6 of the androst-5-ene or androsta-1,5-diene moieties or, alternatively, because unreactive towards the selected amine.

Therefore, with the aim to find a synthetic approach for preparing 17β-carboxamido-4-azasteroids by condensing an amine with an activated 17β-carboxy-4-azasteroid, being the said activated group unreactive towards other functional groups present in the molecule, we noticed that imidazolide derivatives could be successfully used.

However, steric hindered or low nucleophilic and hence scarcely reactive amines did not react at all with 17β-carbonylimidazole-4-azasteroids or, alternatively, enabled to prepare the expected amides in yields even lower than 20%.

For instance, as reported by A. Bhattacharya et al. in Synthetic Communications, 30(17), 2683–2690 (1990), the direct condensation of 3-oxo-4-aza-androst-1-ene-17β-acylimidazole with tert-butylamine so as to get the corresponding amide was unsuccessful, even under extreme reaction conditions.

Likewise, with the aim to prepare fluorinated amides, the condensation between 3-oxo-4-aza-androst-5-ene-17β-carbonylimidazole and the fluorinated amine did not enabled us to get the corresponding amide even operating under drastic conditions, i.e. under pressure in autoclave. EP-A-0367502, in the name of Merck & Co. Inc., discloses a process for preparing 3-oxo-4-azasteroids, among which 17β-carboxamido derivatives are comprised, by reacting the corresponding 17β-carbonylimidazole intermediate with a suitable amine in the presence of a Grignard reagent.

However, it is well-known to the man skilled in the art that when using Grignard reagents, in particular on industrial scale, severe precautions so as to avoid the risks of hazardous reactions are required.

Therefore, although affording the desired amide in high yields, the industrial application of the aforementioned process could present some remarkable drawbacks.

In addition, the same methodology failed to achieve fluorinated 17β-carboxamides in acceptable yields and purity.

In this respect, we have surprisingly found that the said imidazolide derivatives could be unexpectedly converted into the desired amide, under mild conditions, in the presence of acids.

Therefore, it is the object of the present invention a process for preparing the compounds of formula

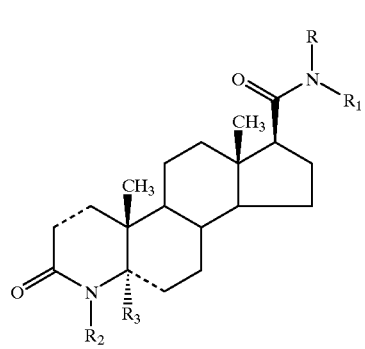

(I)

wherein
the dotted lines - - -, independently from each other, represent a single or double bond;
R and $R_1$, the same or different, represent a hydrogen atom or a straight or branched $C_1$–$C_6$ alkyl, phenylalkyl, alkylphenyl or alkylphenylalkyl group, being the said alkyl groups substituted by one or more fluorine atoms;
$R_2$ is a hydrogen atom or a $C_1$–$C_4$ alkyl group optionally substituted by one or more fluorine atoms;
$R_3$, whenever present, is a hydrogen atom;
provided that at least one of R and $R_1$ contain one or more fluorine atoms and that when the dotted line in position 5,6 represents a double bond, $R_3$ is absent;
which comprises reacting an imidazolide derivative of formula

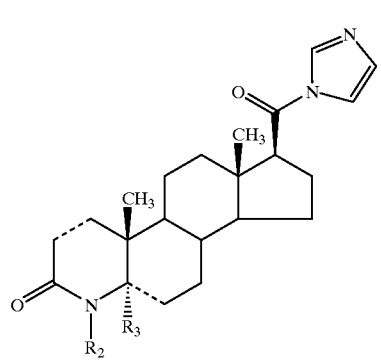

(II)

wherein
the dotted lines, $R_2$ and $R_3$ have the above reported meanings;

with an anhydrous acid, in the presence of an amine of formula $$HN(R)R_1 \quad (III)$$

wherein R and $R_1$ have the above reported meanings; and, if desired, hydrogenating the resultant compound of formula (I) wherein one of both the dotted lines represent a double bond.

The process object of the present invention allows to prepare the compounds of formula (I) in mild conditions and, even more important, it enables to obtain compounds of formula (I) from scarcely reactive amines such as low nucleophilic and/or sterically hindered amines, e.g. fluorinated and even bulky fluorinated amines.

In the present description, unless otherwise specified, with the term straight or branched $C_1$–$C_4$ or $C_1$–$C_6$, alkyl group we intend a methyl, ethyl, n.propyl, isopropyl, n.butyl, sec-butyl, isobutyl, tert-butyl, n.pentyl, n.hexyl and the like.

With the term straight or branched $C_1$–$C_6$ phenylalkyl, alkylphenyl or alkylphenylalkyl group we intend a phenyl group bonded to a straight or branched $C_1$–$C_6$ alkyl moiety as above indicated.

With the term anhydrous acid we conventionally intend an acid with a very low content of water, being the said acid a mineral acid, a strong organic acid or a Lewis acid.

Examples of mineral or strong organic acids are hydrogen chloride, hydrogen bromide, sulphuric acid, methanesulphonic acid, p.toluenesulphonic acid, triflic acid, camphorsulphonic acid, or the like.

Examples of Lewis acids are, for instance, zinc chloride, zinc bromide, aluminium chloride, aluminium bromide, ferric chloride, ferric bromide or the like.

For a general reference to the said acids and, in particular, to Lewis acids see, for instance, J. March, Advanced Organic Chemistry, IV ed. 1992, John Wiley & Sons, Chapter 8, pages 248–272.

In the formulae (I–II) as above, the dotted line ( . . . ) in position 5 indicates a substituent in the α-configuration, i.e. below the plane of the ring, and the wedged lines in position 10, 13 and 17 () indicate a substituent in the β-configuration, i.e. above the plane of the ring.

Preferred compounds prepared according to the process of the present invention are the compounds of formula (I) wherein one of R and $R_1$ is a hydrogen atom and the other is a straight or branched $C_1$–$C_4$ alkyl, phenylalkyl or alkylphenylalkyl group, substituted by at least a fluorine atom in the alkyl moiety.

Even more preferred compounds, in this class, are the compounds of formula (I) wherein the said alkyl groups are $C_1$–$C_3$ perfluoroalkyl groups such as, for instance, trifluoromethyl, 1,1,1-trifluoroethyl, 1,1,1,2,2-pentafluoroethyl or 1,1,1,3,3,3-hexafluoropropyl groups.

The process according to the present invention is preferably carried out to prepare one of the following 17β-carboxamido-4-azasteroids:

1) N-(1,1,1,3,3,3-hexafluoro-2-phenylprop-2-yl)-3-oxo-4-aza-5α-androst-1-ene-17β-carboxamide;
2) N-(1,1,1,3,3,3-hexafluoro-2-phenylprop-2-yl)-3-oxo-4-aza-5α-androstane-17β-carboxamide;
3) N-(1,1,1,3,3,3-hexafluoro-2-phenylprop-2-yl)-3-oxo-4-azaandrost-1,5-diene-17β-carboxamide;
4) N-(1,1,1,3,3,3-hexafluoro-2-phenylprop-2-yl)-3-oxo-4-azaandrost-5-ene-17β-carboxamide;
5) N-[1,1,1,3,3,3-hexafluoro-2-(p-methylphenyl)prop-2-yl]-3-oxo-4-aza-5α-androst-1-ene-17β-carboxamide;
6) N-[1,1,1,3,3,3-hexafluoro-2-(p-methylphenyl)prop-2-yl]-3-oxo-4-aza-5α-androstane-17β-carboxamide;
7) N-[1,1,1,3,3,3-hexafluoro-2-(p-methylphenyl)prop-2-yl]-3-oxo-4-azaandrost-1,5-diene-17β-carboxamide;
8) N-([1,1,1,3,3,3-hexafluoro-2-(p-methylphenyl)prop-2-yl]-3-oxo-4-azaandrost-5-ene-17β-carboxamide;
9) N-(1,1,1-trifluoro-2-phenylprop-2-yl)-3-oxo-4-aza-5α-androst-1-ene-17β-carboxamide;
10) N-(1,1,1-trifluoro-2-phenylprop-2-yl)-3-oxo-4-aza-5α-androstane-17β-carboxamide;
11) N-(1,1,1-trifluoro-2-phenylprop-2-yl)-3-oxo-4-azaandrost-1,5-diene-17β-carboxamide;
12) N-(1,1,1-trifluoro-2-phenylprop-2-yl)-3-oxo-4-azaandrost-5-ene-17β-carboxamide;
13) N-[1,1,1-trifluoro-2-(p-methylphenyl)prop-2-yl]-3-oxo-4-aza-5α-androst-1-ene-17β-carboxamide;
14) N-[1,1,1-trifluoro-2-(p-methylphenyl)prop-2-yl]-3-oxo-4-aza-5α-androstane-17β-carboxamide;
15) N-[1,1,1-trifluoro-2-(p-methylphenyl)prop-2-yl]-3-oxo-4-azaandrost-1,5-diene-17β-carboxamide; 16) N-[1,1,1-trifluoro-2-(p-methylphenyl)prop-2-yl]-3-oxo-4-azaandrost-5-ene-17β-carboxamide.

The process according to the present invention is carried out by reacting a 17β-carbonyl-imidazole derivative of formula (II) with an anhydrous acid in the presence of an amine of formula (III), under inhert atmosphere.

As set forth above, examples of acids are, for instance, gaseous hydrogen chloride or hydrogen bromide as well as sulphuric acid, methanesulphonic acid, triflic acid, p.toluenesulphonic acid, camphorsulphonic acid, or Lewis acids such as zinc chloride, zinc bromide, aluminium chloride, aluminium bromide, ferric chloride and ferric bromide.

Preferably, the said acids are gaseous mineral or strong organic acids.

Even more preferred acids are methanesulphonic acid or hydrogen chloride.

The said acids are used at least in stoichiometric amounts or, preferably, in a molar ratio imidazolide derivative:acid= 1:2.

Larger excesses of acid are equally effective but useless. The reaction is carried out by adding the selected acid to a solution of the imidazolide derivative of formula (II) and of the amine of formula (III) into a suitable solvent at a temperature comprised from room temperature to the refluxing temperature of the reaction mixture for a time varying from 1 hour to 12 hours.

A reaction temperature comprised between 40° C. and 70° C. is preferably selected.

Suitable solvents are chlorinated $C_1$–$C_3$ hydrocarbons such as, for instance, methylene chloride, chloroform or 1, 2-dichloroethane, as well as acetonitrile, tetrahydrofuran or optionally substituted aromatic hydrocarbons such as, for instance, toluene, fluorobenzene, α,α, α-trifluorotoluene or the like.

Preferably, the process of the present invention is carried out starting from the imidazolide derivatives of formula (II) containing a sole double bond in position 5,6 of the steroid moiety.

The imidazolide derivatives of formula (II) as above, wherein the dotted line in position 1,2 represents a single bond and the dotted line in position 5,6 represents a double bond are new and represent a further object of the present invention.

In a further variant of the process, the imidazolide derivative of formula (II), dissolved in the aforementioned solvents, is firstly reacted with the said anhydrous acid. The supposed addition salt of the imidazolide derivative of formula (II) is then reacted in situ, and hence without the need of being isolated and further purified, with a suitable amine of formula (III) so as to get the expected 17β-carboxamido-4-azasteroid of formula (I).

This reaction is performed by directly mixing the salt and the proper amine in the same reaction system, at a temperature comprised between room temperature and the reflux temperature of the reaction mixture, for a time varying from 1 hour to 12 hours.

A reaction temperature comprised between 40° C. and 70° C. is preferably selected.

The compounds of formula (I) are thus obtained in good yields and are easily recovered and purified according to conventional methods.

The starting materials of formula (II) are prepared according to conventional methods by reacting the corresponding carboxylic acid, optionally in the activated form, with an imidazole derivative such as, for instance, carbonyl-diimidazole, oxalyl-diimidazole or sulphonyl-diimidazole.

For a general reference to the preparation of the compounds of formula (II) see, for instance, the aforementioned WO 94/03475 and EP-A-0367502.

The 4-azaandrost-5-ene-17β-carbonylimidazole derivatives of formula (II), being novel, are prepared as above indicated by reacting a 3-oxo-4-azaandrost-5-ene-17β-carboxylic acid of formula

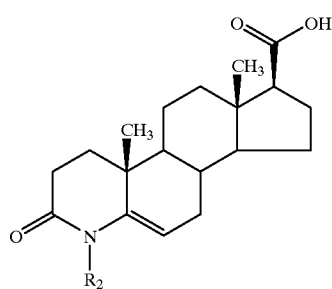

(IV)

wherein
R$_2$ represents a hydrogen atom or a C$_1$–C$_4$ alkyl group optionally substituted by one or more fluorine atoms;
with carbonyl-diimidazole, sulphonyl-diimidazole or oxalyl-diimidazole, according to what reported in the literature (see, for instance, Angew. Chem. 1962, 74, 407).

For a reference to the preparation of the carboxylic acid derivatives of formula (IV) see, for instance, the process disclosed in WO 90/15045 in the name of Upjohn & Co.

Also the amines of formula (III) are known or easily prepared according to known methods as reported, for instance, in the aforementioned WO 94/03475.

By starting from the proper derivative of formula (II) having one two or no double bonds on the steroid moiety, the corresponding carboxamido-4-azasteroid of formula (I) are thus obtained.

To this extent, it is clear to the man skilled in the art that by hydrogenating a compound of formula (I) having one or two double bonds, according to the present invention, the corresponding saturated compounds of formula (I) wherein both dotted lines represent a single bond, are obtained.

The said hydrogenation step is carried out according to conventional techniques.

As an example, the hydrogenation can be carried out in a suitable solvent such as methanol, ethanol or acetic acid, in the presence of about 10% to 30% of conventional hydrogenation catalysts such as, for instance, palladium-, platinum- or rhodium-based catalysts, under a hydrogen pressure of about 3 to 7 atmospheres at a temperature comprised between room temperature and 50° C. for a time varying from half a hour to 18 hours.

In a preferred embodiment of the present invention, a compound of formula (I) such as, for instance, N-(1,1,1,3,3,3-hexafluoro-2-phenylprop-2-yl)-3-oxo-4-aza-5α-androstane-17β-carboxamide, as a useful therapeutic agent, is prepared by reacting a 3-oxo-4-azaandrost-5-ene-17β-carboxylic acid derivative of formula (IV), in a suitable solvent such as dimethylformamide, with a proper amount of 1,1'-carbonyl-diimidazole.

The reaction mixture is kept under stirring at a temperature of 60° C. for a period of 4 h hours.

The 3-oxo-4-azaandrost-5-ene-17β-carbonylimidazole of formula (II) thus prepared, admixed with a proper amount of 1,1,1,3,3,3-hexafluoro-2-phenylprop-2-yl-amine of formula (III), is then treated slowly under nitrogen atmosphere at 60° C. and under good stirring with a proper amount of an anhydrous strong acid such as anhydrous methanesulphonic acid. The reaction mixture is maintained at 60° C. for 6 hours under stirring.

The thus obtained N-(1,1,1,3,3,3-hexafluoro-2-phenylprop-2-yl)-3-oxo-4-azaandrost-5-ene-17β-carboxamide of formula (I), isolated and purified according to conventional techniques, is then catalytically hydrogenated, for instance into a Parr apparatus or into an autoclave in the presence of catalytic amounts of 5% Pt on charcoal, to get N-(1,1,1,3,3,3-hexafluoro-2-phenylprop-2-yl)-3-oxo-4-aza-5α-androstane-17β-carboxamide of formula (I).

The process object of the present invention provides a very advantageous synthetic route to prepare 17β-carboxamido-4-azasteroid derivatives, in good yields and under mild operating conditions, by starting from known or easily prepared compounds and even without the need of isolating the reaction intermediates.

Moreover, it allows to prepare amides from sterically hindered and/or low nucleophilic and hence scarcely reactive amines.

With the aim of better illustrating the present invention, without limiting it, the following examples are now given.

EXAMPLE 1

Preparation of 3-oxo-4-azaandrost-5-ene-17β-carbonyl-1-imidazole 1,1-Carbonyldiimidazole (70.5 g; 0.435 mol) was added to a vigorously stirred suspension of 3-oxo-4-azaandrost-5-ene-17β-carboxylic acid (115 g; 0.362 mol) in N,N-dimethylformamide (1.44 l). The mixture was heated to 60° C. for 4 h and a precipitate was formed.

The reaction mixture was concentrated under vacuum and diluted with ethyl acetate; the precipitate was filtered, washed with ethyl acetate and dried under vacuum at 40° C.

to afford 3-oxo-4-azaandrost-5-ene-17β-carbonyl-1-imidazole (116.7 g) as a light yellow solid.

By repeating the same treatment on the mother liquors a second crop of compound (7.23 g) was obtained. The total yield was 93.07% (m.p. 284–8° C. with decomposition; purity >98% by HPLC analysis).

NMR (CDCl$_3$) δ (ppm): 8.18 (s, 1H, H(2')) 8.10 (bs, 1H, NH(4)), 7.60 (s, 1H, H(5')), 7.10 (s, 1H, H(4')), 4.81 (m, 1H, H(6)), 1.11 (s, 3H, Me(19)), 0.78 (s, 3H, Me(18))

EXAMPLE 2
Preparation of N-(1,1,1,3,3,3-hexafluoro-2-phenylprop-2-yl)-3-oxo-4-azaandrost-5-ene-17β-carboxamide 3-Oxo-4-azaandrost-5-ene-17β-carbonyl-1-imidazole (29.05 g; 79.05 mmol) was dissolved in chloroform (174 ml) under nitrogen atmosphere at room temperature.

1,1,1,3,3,3-Hexafluoro-2-phenylprop-2-ylamine (38.45 g; 158.11 mmol) was therein added in one portion.

The temperature of the reaction mixture was raised to 60° C. and, under vigorous stirring, methanesulphonic acid (0.26 ml; 58.11 mmol) was added dropwise. The mixture was stirred at 60° C. for 6 hours under nitrogen atmosphere and then cooled to room temperature, washed thoroughly with 0.5 N NaOH (300 ml +250 m), with brine and dried over anhydrous sodium sulphate. After evaporating the solvent under vacuum, a yellowish solid (51.56 g) was obtained.

The crude was purified by treatment with ethyl acetate at reflux, concentration and precipitation by addition of tert-butylmethyl ether to afford, after suction filtration and drying at 40° C. under vacuum, N-(1,1,1,3,3,3-hexafluoro-2-phenylprop-2-yl)-3-oxo-4-azaandrost-5-ene-17p-carboxamide (20.38 g; m.p. 251–3° C. with decomposition; purity: 99.11% by HPLC analysis).

From the mother liquors by means of an analogous treatment a second crop of compound (9.20 g; purity: 98% by HPLC analysis) was obtained, raising the total yield to 69%.

NMR (CDCl$_3$) δ (ppm): 7.60–7.37 (m, 6H, Ph+NH(4) ), 5.83 (s, 1H, NH(21)), 4.81 (m, 1H, H(6)), 1, 11 (s, 3H, Me(19)), 0.76 (s, 3H, Me(18)).

EXAMPLE 3
Preparation of N-(1,1,1,3,3,3-hexafluoro-2-phenylprop-2-yl)-3-oxo-4-aza-5α-androstane-17β-carboxamide A solution of N-(1,1,1,3,3,3-hexafluoro-2-phenylprop-2-yl)-3-oxo-4-azaandrost-5-ene-17β-carboxamide (23.04 g; 42.46 mmol) in glacial acetic acid (460 ml) was hydrogenated in autoclave in the presence of 5% Palladium on charcoal (23.0 g), under a pressure of 7 bar of hydrogen at 50° C.

The mixture was cooled to room temperature, the catalyst was filtered off and the filtrate was poured into water (3 1). After neutralisation with 15% NaOH, the solid was collected by suction filtration, washed thoroughly with water and dried at 50° C. under vacuum.

N-(1,1,1,3,3,3-hexafluoro-2-phenylprop-2-yl)-3-oxo-4-aza-5α-androstane-17β-carboxamide (21.36 g; yield: 91.95%) was obtained as a white solid (m.p. 254–8° C. with decomposition).

NMR (CDCl$_3$) δ: 7.50–7.30 (m, 5H, Ph), 5.88 (bs, 1H, NH(21)), 5.42 (bs, 1H, NH(4)), 3.08 (dd, 1H, H(5a)), 2.42 (m, 2H, CH$_2$(2)), 0.90 (s, 3H, Me(19)), 0.76 (s, 3H, Me(18)).

EXAMPLE 4

Preparation of 3-oxo-4-aza-5α-androst-1-ene-17β-carbonyl-1-imidazole 1,1'-Carbonyldiimidazole (2.00 g; 12.36 mmcol) and 3-oxo-4-aza-5α-androst-1-ene-17β-carboxylic acid (3.14 g; 9.89 mmol) were suspended in N,N'-dimethylformamide (37 mL) under argon. The mixture was heated to 65° C. for 4 h. The solid at first dissolved then a new precipitate was formed. After cooling, the solvent was evaporated under vacuum and the resulting thick suspension was diluted with methyltertbutylether. After storage at +4° C. for 48 h the solid was filtered by suction filtration, washed with methyltertbutylether and dried at 50° C. under vacuum. There were obtained 2.97 g (81.8%) of light brown solid.

NMR (CDCl$_3$) δ (ppm): 8.43 (s, 1H, H(2')), 7.71 (s, 1H, H(5')), 7.40 (bs, 1H, NH(4)), 7.05 (s, 1H, H(4')), 6.77 (d, 1H, H(1)) 5.57 (dd, 1H, H(2)), 3.42 (t, 1H, H(17)), 3.17 (dd, 1H, H(5α)), 0.82 (s, 3H, Me(19)), 0.63 (s, 3H, Me(18)).

EXAMPLE 5

Preparation of N-(1,1,1,3,3,3-hexafluoro-2-phenylprop-2-yl)-3-oxo-4-aza-5α-androst-1-ene-17β-carboxamide To a suspension of 3-oxo-4-aza-5α-androst-1-ene-17β-carbonyl-1-imidazole (2.97 g; 8.08 mmol) in chloroform (17.8 mL) the 1,1,1,3,3,3-hexafluoro-2-phenylprop-2-yl amine (hexafluorocumylamine) (3.93 g; 16.16 mmol) was added under argon. The temperature was raised to 50° C. and methanesulphonic acid (1.05 mL; 16.16 mmol) was added dropwise; then the slightly brown mixture was stirred for 7.5 h at 60° C. After cooling to room temperature, the suspension was filtered on a Gooch funnel and the panel was washed with methylene chloride (10 mL); the clear filtrate was evaporated to dryness under vacuum, dissolved in tetrahydrofurane (16 mL) and treated with 2M NaOH under good stirring for 1 h. The mixture was then diluted with water (50 mL) and extracted with ethyl acetate (3×25 mL). The collected organic extracts were washed with 0.5M NaOH (20 mL) dried over sodium sulphate and the solvent was evaporated under vacuum to afford 5.63 g of row product.

The row product was purified by crystallization from ethyl acetate and methyltertbutylether, dried in an oven at 50° C. for several hours, to yield 2.69 g (61.4%) of pure white solid compound (m.p. 218–222° C.).

NMR (CDCl$_3$) δ (ppm): 7.38–7.54 (m, 5H, Ph), 6.79 (d, 1H, H(1)), 5.89 (s, 1H, NH(21)), 5.82 (dd, 2H, H(2)), 5.39 (s, 1H, NH(4) ), 3.33 (dd, 1H, H(5α)), 0.98 (s, 3H, Me(19)), 0.76 (s, 3H, Me(18) ).

MS (FAB⁻) (m/z) 541[M-H]⁻, 471 [M-CHF₃]⁻.

What is claimed is:

1. A process for producing a compound of formula

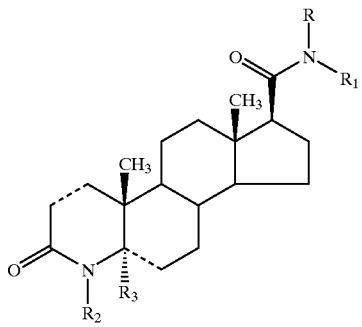

(I)

wherein the dotted lines - - - , independently from each other, represent a single or double bond;

R and R₁, which are the same or different, each represents hydrogen or a straight or branched C₁–C₆, alkyl, phenylalkyl, alkylphenyl or alkylphenylalkyl group, the said alkyl groups being unsubstituted or substituted by one or more fluorine atoms;

R₂ is hydrogen or a C₁–C₄ alkyl group optionally substituted by one or more fluorine atoms;

R₃, whenever present, is a hydrogen atom;

provided that at least one of R and R₁ contains one or more fluorine atoms and that, when the dotted line at position 5,6 represents a double bond, R3 is absent;

which process comprises reacting an imidazolide derivative of formula

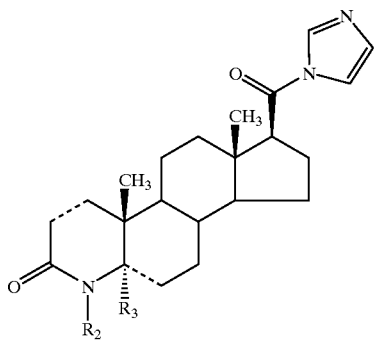

(II)

wherein the dotted lines, R₂ and R₃ are as defined above, with an anhydrous acid in the presence of an amine of formula

HN(R)R₁ (III)

wherein R and R₁ are as defined above; and, if desired, hydrogenating a resultant compound of formula (I) wherein one or both of the dotted lines represents a double bond.

2. A process according to claim 1 wherein the anhydrous acid is selected from mineral acids, strong organic acids and Lewis acids.

3. A process according to claim 1 wherein the anhydrous acid is methanesulphonic acid or hydrogen chloride.

4. A process according to claim 1 wherein in formula (I), one of R and R₁ is hydrogen and the other is a straight or branched C₁–C₄ alkyl, phenylalkyl or alkylphenylalkyl group, substituted by at least one fluorine atom in the alkyl moiety.

5. A process according to claim 1 wherein, in formula (II), the dotted line at position 1,2 represents a single bond and the dotted line at position 5,6 represents a double bond.

6. A process according to claim 1 wherein the compound of formula (I) is selected from:

N-(1,1,1,3,3,3-hexafluoro-2-phenylprop-2-yl)-3-oxo-4-aza-5α-androst-1-ene-17β-carboxamide;

N-(1,1,1,3,3,3-hexafluoro-2-phenylprop-2-yl)-3-oxo-4-aza-5α-androstane-17β-carboxamide;

N-(1,1,1,3,3,3-hexafluoro-2-phenylprop-2-yl)-3-oxo-4-azaandrost-1, 5-diene-17β-carboxamide;

N-(1,1,1,3,3,3-hexafluoro-2-phenylprop-2-yl)-3-oxo-4-azaandrost-5-ene-17β-carboxamide;

N-[1,1,1,3,3,3-hexafluoro-2-(p-methylphenyl)prop-2-yl]-3-oxo-4-aza-5α-androst-1-ene-17β-carboxamide;

N-[1,1,1,3,3,3-hexafluoro-2-(p-methylphenyl)prop-2-yl]-3-oxo-4-aza-5α-androstane-17β-carboxamide;

N-[1,1,1,3,3,3-hexafluoro-2-(p-methylphenyl)prop-2-yl]-3-oxo-4-azaandrost-1,5-diene-17β-carboxamide;

N-[1,1,1,3,3,3-hexafluoro-2-(p-methylphenyl)prop-2-yl]-3-oxo-4-azaandrost-5-ene-17β-carboxamide;

N-(1,1,1-trifluoro-2-phenylprop-2-yl)-3-oxo-4-aza-5α-androst-1-ene-17β-carboxamide;

N-(1,1,1-trifluoro-2-phenylprop-2-yl)-3-oxo-4-aza-5α-androstane-17β-carboxamide;

N-(1,1,1,-trifluoro-2-phenylprop-2-yl)-3-oxo-4-azaandrost-1,5-diene-17β-carboxamide;

N-(1,1,1-trifluoro-2-phenylprop-2-yl)-3-oxo-4-azaandrost-5-ene-17β-carboxamide;

N-[1,1,1-trifluoro-2-(p-methylphenyl)prop-2-yl]-3-oxo-4-aza-5α-androst-1-ene-17β-carboxamide;

N-[1,1,1-trifluoro-2-(p-methylphenyl)prop-2-yl]-3-oxo-4-aza-5α-androstane-17β-carboxamide;

N-[1,1,1-trifluoro-2-(p-methylphenyl)prop-2-yl]-3-oxo-4-azaandrost-1,5-diene-17β-carboxamide; and N-[1,1,1-trifluoro-2-(p-methylphenyl)prop-2-yl]-3-oxo-4-azaandrost-5-ene-17β-carboxamide.

7. A process for producing a compound of formula (I):

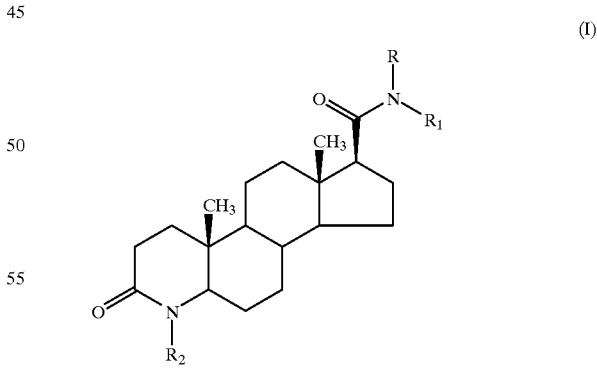

(I)

wherein one of R and R₁ represents hydrogen and the other is a C₁–C₄ phenylalkyl group substituted by one or more fluorine atoms; and R₂ is hydrogen or a C₁–C₄ alkyl group optionally substituted by one or more fluorine atoms;

which process comprises (i) reacting a compound of formula (IV):

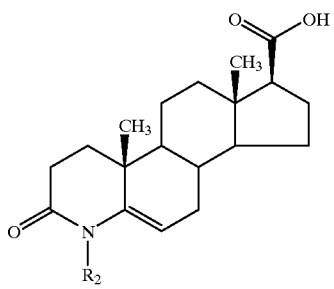

(IV)

wherein $R_2$ is as defined above,
with carbonyl-diimidazole, oxalyl-diimidazole or sulphonyl-diimidazole so as to obtain an imidazolide derivative of formula (II):

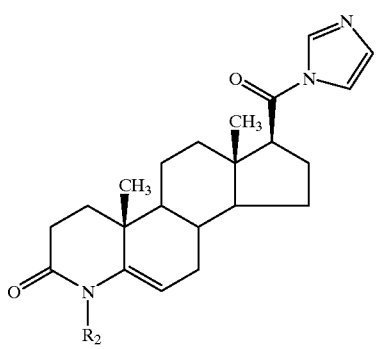

(II)

wherein $R_2$ is as defined above;

(ii) reacting the said compound of formula (II) with anhydrous methanesulphonic acid or hydrogen chloride in the presence of an amine of formula $$HN(R)R_1 \qquad (III)$$

wherein one of R and $R_1$ represents hydrogen atom and the other is a $C_1$–$C_4$ phenylalkyl group substituted by one or more fluorine atoms; and (iii) hydrogenating the resultant compound of formula (I):

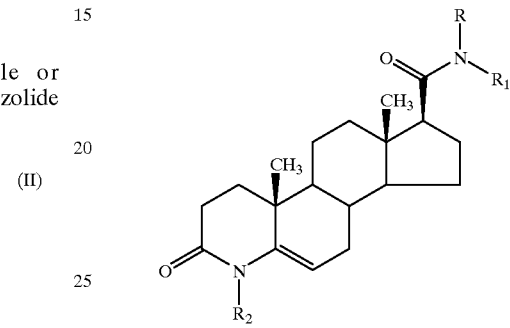

(I)

wherein R, $R_1$ and $R_2$ are as defined above.

8. A process according to claim 2, wherein the anhydrous acid is methanesulfonic acid or hydrogen chloride.

* * * * *